United States Patent
Di Fabrizio et al.

(10) Patent No.: US 7,535,564 B2
(45) Date of Patent: May 19, 2009

(54) APPARATUS FOR DETERMINING THE INTERNAL OUTLINE OF A DUCT OR CAVITY, AND IN PARTICULAR FOR DETERMINING THE INTERNAL IMPRESSION OF THE AUDITORY CANAL, A PROBE FOR THIS APPARATUS, AND REFLECTION DEVICE FOR AN OPTICAL SCANNING APPARATUS

(75) Inventors: Enzo Di Fabrizio, Trieste (IT); Stefano Cabrini, Anguillara Sabazia (IT); Danut Adrian Cojoc, Trieste (IT); Luca Businaro, Trieste (IT)

(73) Assignee: INFM Istituto Nazionale per La Fisica Della Materia, Genova (IT)

( * ) Notice: Subject to any disclaimer, the term of this patent is extended or adjusted under 35 U.S.C. 154(b) by 245 days.

(21) Appl. No.: 10/517,657

(22) PCT Filed: Jun. 12, 2003

(86) PCT No.: PCT/IT03/00366

§ 371 (c)(1),
(2), (4) Date: Dec. 13, 2004

(87) PCT Pub. No.: WO03/105685

PCT Pub. Date: Dec. 24, 2003

(65) Prior Publication Data

US 2006/0074509 A1     Apr. 6, 2006

(30) Foreign Application Priority Data

Jun. 14, 2002   (IT) .......................... TO2002A0515

(51) Int. Cl.
  *G01N 21/00* (2006.01)
(52) U.S. Cl. .............. 356/241.1; 356/241.3; 356/241.4; 356/241.5; 356/241.6
(58) Field of Classification Search ........................ None
See application file for complete search history.

(56) References Cited

U.S. PATENT DOCUMENTS 5,487,012 A    1/1996   Tophelm et al.

(Continued)

FOREIGN PATENT DOCUMENTS

BE          1 010 200 A      3/1998
WO       WO 02/091920      11/2002

OTHER PUBLICATIONS

Xie Huikai et al.: "A SCS SMOS Micromirror for Optical Coherence Tomographic Imaging" Technical Digest., MEMS 2002 IEEE International Conference on Micro Electro Mechanical Systems, Las Vegas, NV, USA, Jan. 20, 2002-Jan. 24, 2002, pp. 495-498, XP010577701, Piscataway, NJ, USA, ISBN: 0-7803-7185-2, pp. 497-487, section "OCT application" abstract.
J. Micromech. Microeng. 13, 2003, pp. 383-389.

*Primary Examiner*—Michael P Stafira
(74) *Attorney, Agent, or Firm*—Suhrue Mion, PLLC (57) ABSTRACT

An apparatus for determining the internal outline of a duct or cavity, comprises light-emitting means (71) suitable for generating a collimated light beam, an elongate probe element (51; 51'; 51") suitable for being introduced into the duct and for guiding the collimated beam along a predetermined propagation direction, reflector means (52) supported by the probe element (51; 51'; 51") and suitable for deflecting the collimated beam so as to illuminate the internal wall of the duct, and for deflecting the reflected or diffused light coming from an illuminated point (P) of the internal wall so as to guide it along the probe element (51; 51'; 51"), and detection means (76) suitable for receiving an image of the illuminated point (P), which image is correlated with the optical distance of the point from the detection means (76), and for providing a corresponding electrical signal. The image is formed by the light guided by the receiving reflector means (52). The reflector means comprise a micro-mirror element (52) articulated to a distal end of the probe element (51; 51'; 51"). The micro-mirror element (52) is orientable so as to deflect the collimated beam in selectively different directions.

4 Claims, 4 Drawing Sheets

U.S. PATENT DOCUMENTS 6,485,413 B1 * 11/2002 Boppart et al. ................. 600/16
6,687,010 B1 * 2/2004 Horii et al. ................... 356/479
7,206,067 B2 * 4/2007 Jensen et al. ............. 356/241.1
2001/0022682 A1 9/2001 McClelland
2002/0050744 A1 5/2002 Waelti et al.
2003/0164952 A1 * 9/2003 Deichmann et al. ......... 356/603

* cited by examiner

APPARATUS FOR DETERMINING THE INTERNAL OUTLINE OF A DUCT OR CAVITY, AND IN PARTICULAR FOR DETERMINING THE INTERNAL IMPRESSION OF THE AUDITORY CANAL, A PROBE FOR THIS APPARATUS, AND REFLECTION DEVICE FOR AN OPTICAL SCANNING APPARATUS

This is a National Stage entry of Application No. PCT/IT2003/000366 filed Jun. 12, 2003, the complete the complete disclosure of which is incorporated into this application by reference.

BACKGROUND OF THE INVENTION

The present invention relates to an apparatus for determining the internal outline of a duct or cavity and, in particular, to an apparatus for determining the internal impression of the auditory canal.

It is known that modern internal hearing prostheses have to fit the shape of the user's auditory canal as well as possible. For this purpose, it is necessary to have an accurate copy of the internal impression of the auditory canal. According to conventional techniques, this is achieved by introducing quick-setting mouldable material into the auditory canal. Once the material has set, it is removed from the ear, thus providing a cast of the canal. Finally, the surface of the cast is subjected to a scanning process and is mapped so as to produce data that can be stored by a computer.

For example, U.S. Pat. No. 5,487,012 describes a method for the scanning of a cast of an auditory canal in order to obtain a digital image which is then processed in order to design the hearing prosthesis.

These conventional techniques for determining the internal profile of the auditory canal have some disadvantages, amongst which is their inevitable invasive nature and the complexity and number of steps that are necessary to produce a cast suitable for the manufacture of a mould for the preparation of the outer shell of the hearing prosthesis, since the cast extracted from the ear has to be processed further in order to eliminate its imperfections.

The document WO 02/091920 describes an apparatus for obtaining geometrical data relating to the internal surface of the ear, comprising a probe with a rod portion containing at least one light guide and a light source at the proximal end of the light guide. The apparatus further comprises a distal portion which can be inserted in the ear canal and has means for directing the light onto at least one point of the internal surface of the ear canal. For this purpose, the above-mentioned means comprise a mirror with a conical surface. A probe of this type is quite bulky and inefficient, particularly when the ear canal is tortuous.

SUMMARY OF TILE INVENTION

An object of the invention is to provide an apparatus which can produce a three-dimensional image of the auditory canal automatically whilst avoiding contact of any type with the internal walls of the ear and facilitating the process of producing the final cast.

This object is achieved, according to the invention, by an apparatus for determining the internal outline of ducts and cavities, having the characteristics defined in the claims.

A further object of the present invention is to provide a probe for apparatus for determining the internal profile of ducts and cavities having the characteristics defined in the claims.

This object is achieved, according to the invention, by a probe.

As will be appreciated, although the apparatus according to the invention is particularly suitable for producing an internal impression of the auditory canal, it can be used to produce a three-dimensional map of the internal walls of ducts or cavities of small cross-section and, in particular, those which are quite inaccessible and which have constrictions or partial occlusions.

According to another object of the present invention, a reflection device for optical scanning apparatus having the characteristics defined is proposed.

By virtue of greater lightness and flexibility in comparison with known devices (described, for example, in J. Micromech. Microeng. 13 (2003) 383-389), a device of this type is particularly suitable for use in the apparatus according to the invention.

According to another object of the present invention, a method of producing an internal impression of the auditory canal is proposed.

According to a further object of the present invention, a method for the manufacture of internal hearing prostheses is proposed.

BRIEF DESCRIPTION OF TILE DRAWINGS

Some preferred but non-limiting embodiments of the invention will now be described with reference to the appended drawings, in which.

DETAILED DESCRIPTION OF TILE INVENTION

Figure 1:
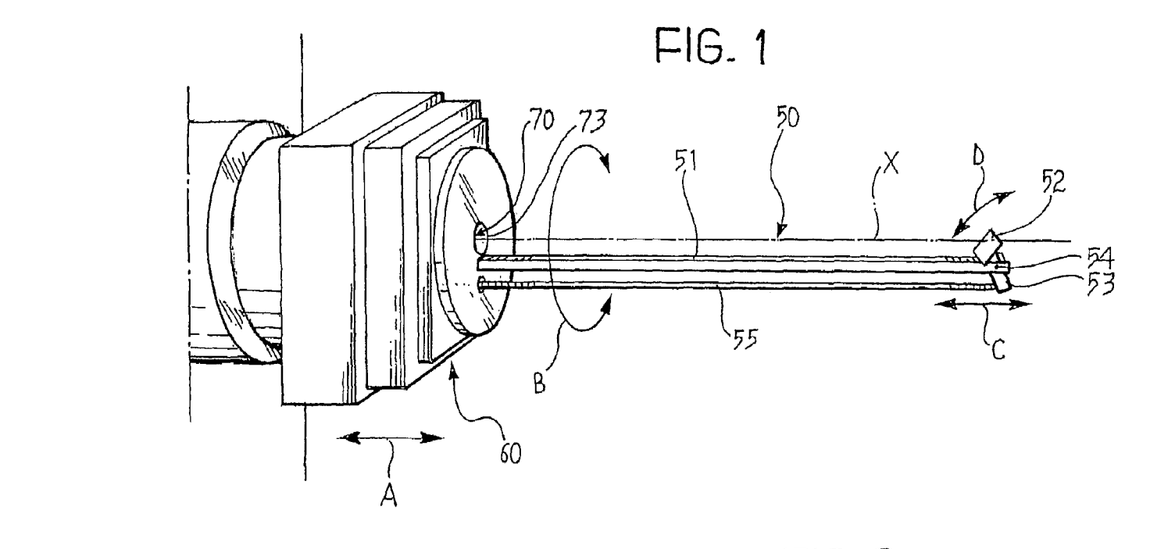
FIG. 1 is a perspective view of a probe for an apparatus for determining the internal outline of ducts and cavities according to the invention.

With reference to FIG. 1, an apparatus for determining the internal profile of ducts and cavities comprises a probe unit 50 suitable for being introduced into the cavity of the duct to be measured. The probe unit 50 comprises a probe arm 51 formed by a rod of small dimensions suitable for supporting a substantially flat micro-mirror 52 by means of a microscopic lever 53. One end of the lever 53 is integral to the body of the micro-mirror 52 and a central portion of the lever is articulated to the distal end of the probe arm 51 by means of a microscopic pin 54. The free end of the lever 53 is connected magnetically to a control rod 55 which is arranged parallel to the probe arm 51 and can slide along its own longitudinal axis. The movement of the rod 55 is brought about by piezoelectric means (not shown) disposed at the proximal end of the rod 55.

The elements of the probe unit 50 are covered with a protective layer produced, for example, by evaporation of plastics materials.

In an apparatus for determining an internal impression of the auditory canal, the Applicant has produced a probe unit 50 of the type described above having a length of about 3 cm and a cross-section of about 2 mm diameter. These components were manufactured by known micromechanical and microlithographic techniques and the micro-mirror 52 was produced by nanolithography techniques.

The probe unit 50 is supported by a drive unit 60 which, with the use of known mechanisms, can move the probe unit 50 rigidly along the longitudinal axis of the probe arm 51 (indicated by the arrow A), can rotate it about the central axis of the optical system (in the direction indicated by the arrow B), and can move the control rod 55 alone along its longitudinal axis (in the direction of the arrow C). The movement of the control rod 55 moves the lever 53 which pivots about the pin 54, inclining the micro-mirror 52 in a plane containing the central axis X of the optical system (in the directions of the arrow D) which will be described below.

Figure 2:
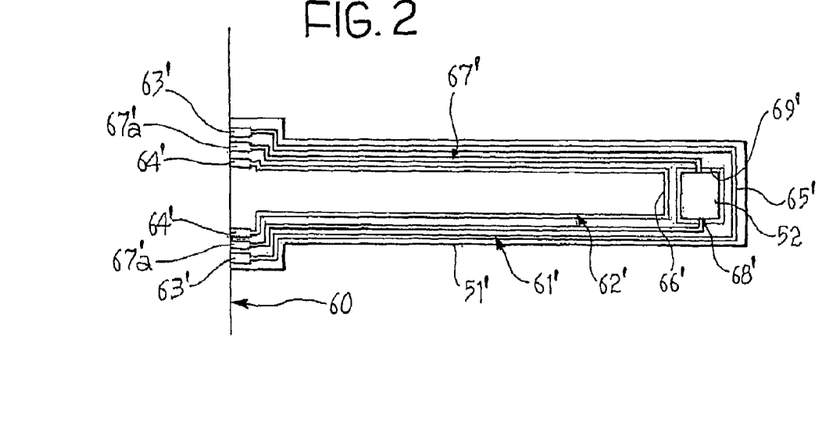
FIG. 2 is a view showing a second embodiment of the probe of FIG. 1 from above.

In a second embodiment of the invention, shown in FIG. 2, the orientation of the micro-mirror 52 is controlled electromagnetically. A plurality of conductive tracks are deposited on a probe arm 51' of a type similar to that described above but made of insulating material. In particular, a first control track and a second control track 61', 62' extend between respective contacts 63', 63'; 64', 64' on the proximal end of the arm 51', the tracks extending along substantially the entire length of the arm 51' and forming respective transverse portions 65', 66' on the distal end of the arm 51'. A central track 67' extends parallel to the tracks 61', 62', remaining interposed between them and extending between contacts 67a', 67a'. The central track 67' forms a transverse portion 68' interposed between the transverse portions 65' and 66' of the control tracks 61', 62'. The micro-mirror 52 is formed integrally with the transverse portion 68'.

Beneath the micro-mirror 52, the probe arm 51' has an opening 69' which has a cross-section larger than that of the micro-mirror 52 and is arranged so as to encompass it completely.

The tracks 61', 62', 67' and the micro-mirror 52 are produced by conventional deposition techniques and the opening 69' is produced by chemical etching techniques, after the deposition of the micro-mirror 52.

The micro-mirror 52 enables the electrical continuity of the transverse portion 68' to be maintained and the portion 68' provides a pin about which the micro-mirror 52 can rotate freely in the opening 69'.

According to this embodiment of the invention, the drive unit 60 can orient the micro-mirror 52 by sending electrical currents to the tracks 61', 62', 67' via the contacts 63', 64' and 67a'. The direction of the currents in the transverse portions 65', 66', 68' determines the direction of rotation of the micro-mirror 52.

A control unit (not shown) controls the drive unit 50 and detects the position and the orientation of the movable elements of the probe unit 50.

With further reference to FIG. 1, a light emitter and a light detector, generally indicated 70, can project a collimated light beam against the micro-mirror 52 and can receive the light reflected by the micro-mirror 52, respectively. The central axis X of the optical system is formed by the straight line which joins the emitter/receiver 70 and the micro-mirror 52. In the condition in which the probe unit 50 is inserted in the duct, the light beam projected by the emitter/receiver 70 and reflected by the micro-mirror 52 falls on the internal walls of the duct or of the cavity. Each point struck by the light beam in turn reflects or diffuses the light. The light which is reflected or diffused along the line of incidence of the light beam reaches the mirror which reflects it towards the emitter/receiver 70.

Figure 3:
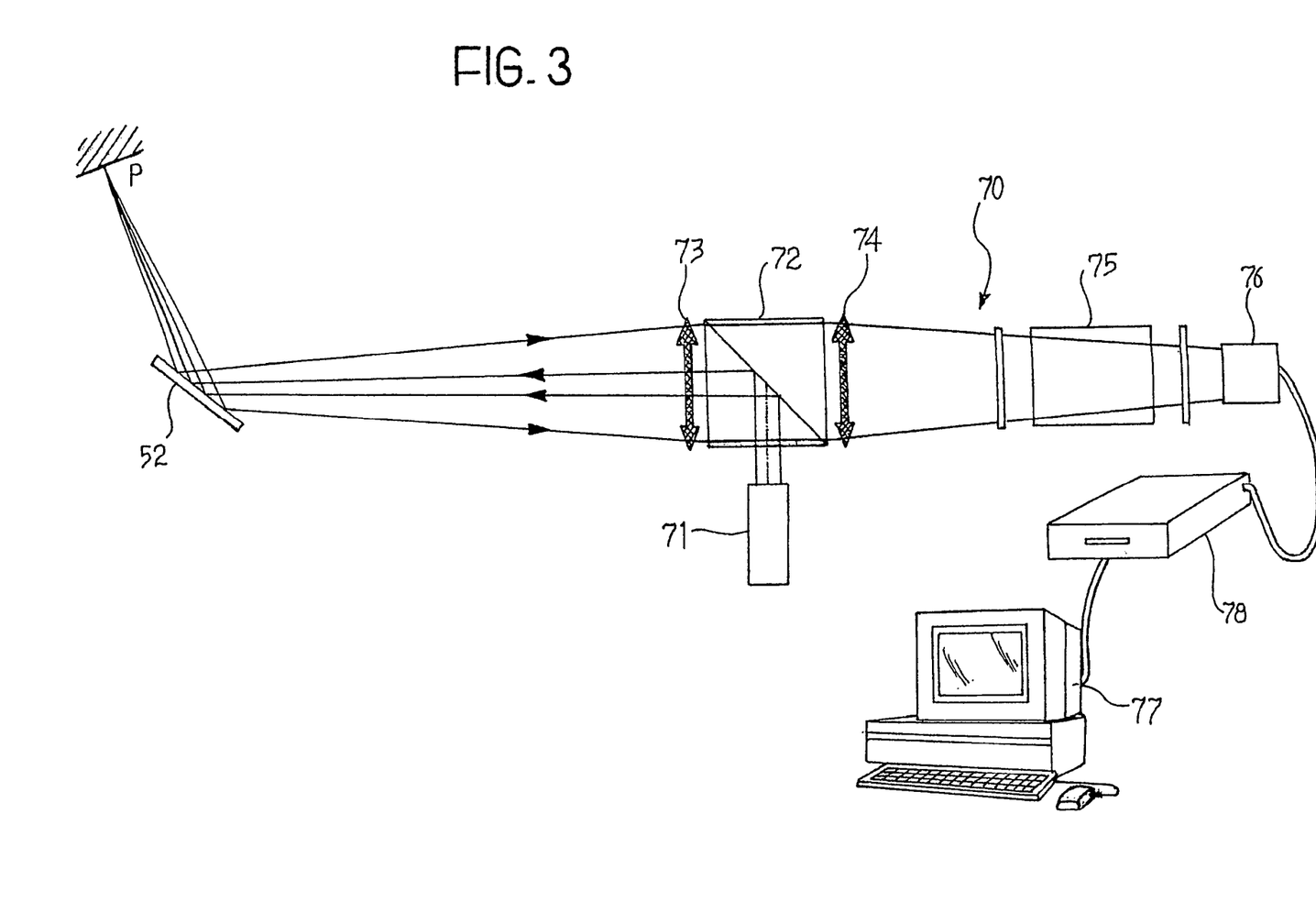
FIG. 3 is a schematic view of an apparatus for determining the internal profile of ducts and cavities according to the invention.

With reference to FIG. 3, this shows schematically the optical arrangement of the emitter/receiver 70. This arrangement is based on conoscopic holography principles. It comprises an almost monochromatic light source 71, for example, a laser, which generates a light beam that is reflected by a semi-reflecting prism 72 and is projected, through an adaptation objective 73, towards the object to be measured, by reflection on the micro-mirror 52. The returning reflected and diffused light re-enters through the adaptation objective 73, after being reflected again by the micro-mirror 52, passes through the semi-reflecting prism 72 and a shaping objective 74, finally reaching a conoscopic module 75 which can produce an interference pattern indicative of the radial distance of the point of incidence of the beam transmitted. This interference pattern is detected by a CCD sensor 76 and transmitted to a processing unit 77 via an interface 78.

Figure 4:
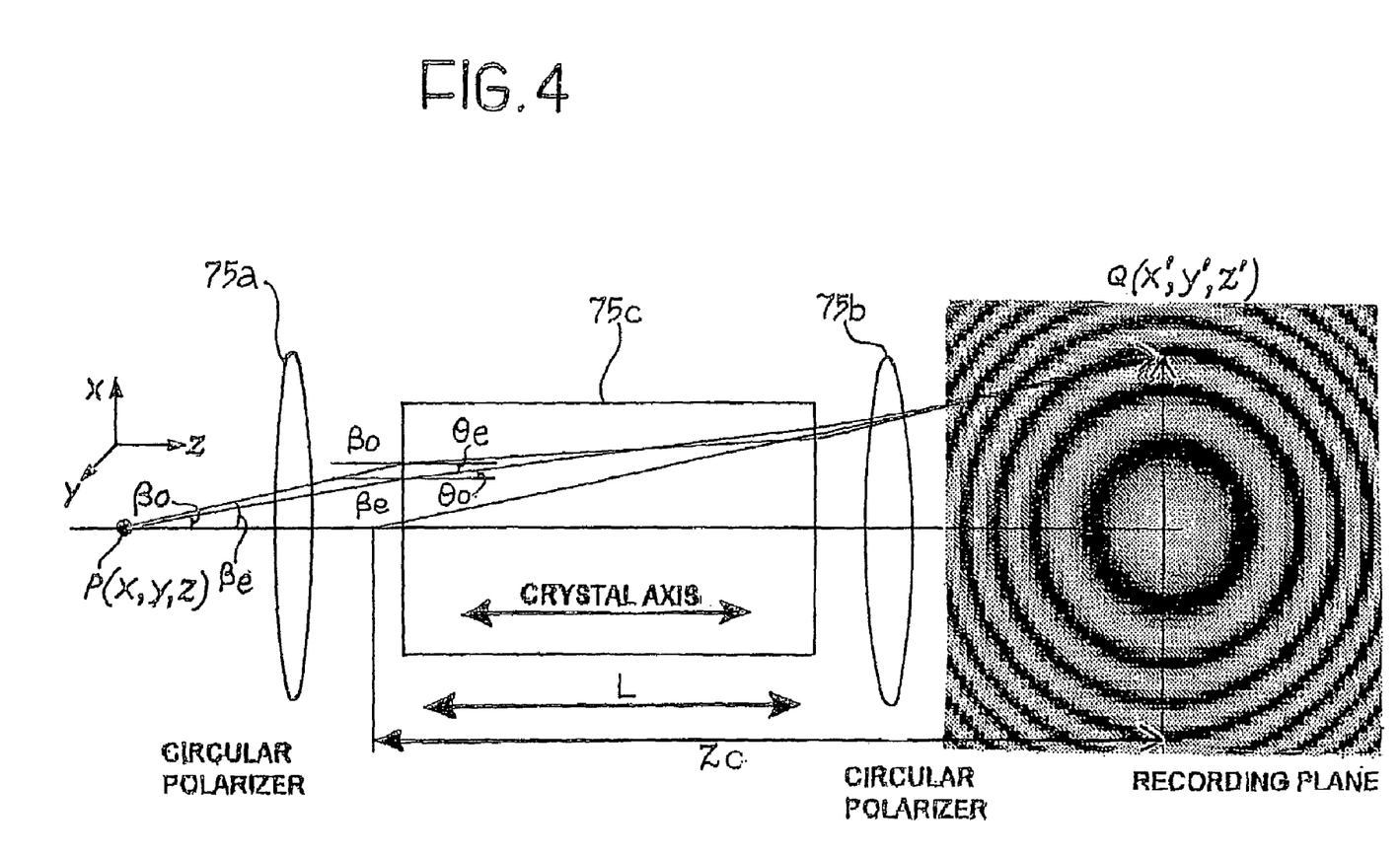
FIG. 4 is a diagram illustrating the operating principle of the apparatus of FIG. 3.

The structure and the principle of operation of the conoscopic module 75 will now be described briefly with reference to FIG. 4. This structure comprises a pair of circular polarizers 75a, 75b between which a crystal (of length L) is interposed so as to produce an interference pattern.

Each object point P struck by the collimated beam (as shown in FIG. 3) diffuses or reflects a non-polarized and spatially incoherent, almost monochromatic light. A ray emerging from the point P at a generic angle β (where β, which is not indicated in the drawing, defines a generic direction of diffusion or reflection) relative to the axis of the optical system passes through the first circular polarizer 75a, which produces two perpendicularly polarized rays that are out of phase by 90°. Within the crystal 75c, the two rays are propagated in accordance with two modes, that is, the ordinary mode and the extraordinary mode, with different velocities ($\beta_o$ and $\theta_o$ indicate the angle between the ordinary ray and the optical axis outside and inside the crystal 75c, respectively, and $\beta_e$ and $\theta_e$ indicate the angle between the extraordinary ray and the optical axis outside and inside the crystal 75c, respectively). In a uniaxial crystal, the ordinary refraction index is constant, whereas the extraordinary refraction index depends on the angle $\theta_e$ between the ray and the optical axis of the crystal and hence on the location of the object point P. When the two rays emerge from the crystal 75c, they are out of phase in accordance with their velocity difference. When they pass through the second polarizer 75b, the two rays regain the same polarization mode. A conoscopic hologram is thus obtained by measuring the intensity of illumination at every point Q of the recording plane of the CCD sensor 76 ($Z_c$ is the intrinsic conoscopic distance, corresponding to the apparent distance between Q in the recording plane and the emission point P). This intensity distribution results from the interference between the ordinary and extraordinary rays. The resulting interference pattern, which is known as a Fresnel zone plate, may be constructive or destructive according to the phase difference of the two rays.

The interference pattern resulting from a point object consists of a set of concentric fringes with an inter-fringe distance which decreases radially outwards. The modulation in intensity I(Q) resulting from the interference between the ordinary and extraordinary rays at the point Q(x', y') is correlated with the intensity I(P) at the object point P(x,y,z) by the equation:

$$I(Q)=I(P)(1+\cos \Delta\phi) \quad (1)$$

where $\Delta\phi$ is the phase difference between ordinary ray and extraordinary ray. Since this phase difference is correlated with the distance of the point P from the recording plane of the CCD sensor 76, it is possible to measure the periods of the fringes of the holograms in order to determine the exact distance from the point measured.

The drive unit 60, controlled by the control unit, guides the translational and/or rotational movement of the probe unit 50 and/or the orientation of the micro-mirror 52, enabling the probe 50 to measure the optical distance of a predetermined quantity of points of the internal wall of the duct such as to enable the outline of the wall to be mapped with the desired accuracy.

Figures 5, 6:
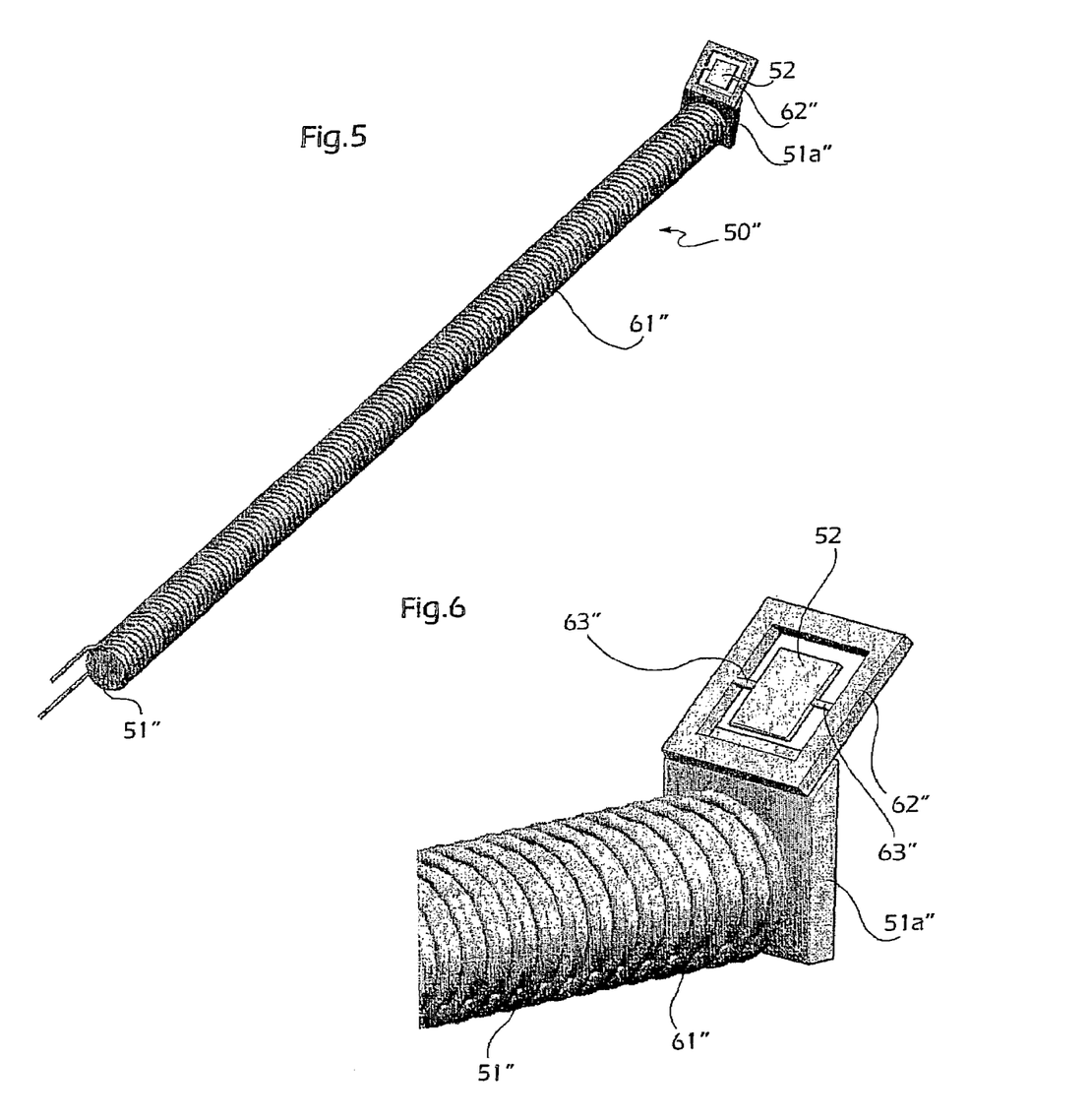
FIG. 5 is a perspective view of a third embodiment of the probe of FIG. 1.
FIG. 6 is a view of a detail of the probe of FIG. 5.

A further embodiment of the present invention is illustrated in FIGS. 5 and 6. A probe unit 50" is supported by a drive unit (not shown) which is similar to the drive unit 60 described with reference to the embodiment of FIG. 1 and which can move the probe unit 50" rigidly along its longitudinal axis and can rotate it about the central axis of the optical system contained in the probe unit 50" and described below.

A winding 61" of wire made of insulated conductive material, for example copper, is disposed on a probe arm 51", preferably along its entire length, the probe arm being of similar type to those described above but of substantially cylindrical shape and made of ferromagnetic material. At its distal end, the arm 51" comprises a support portion 51a" projecting outside the last turns of the winding 61". A frame element 62" of non-magnetic (or magnetically insulating) material is fixed to the support portion 51a". A micro-mirror 52, formed by a self-supporting film of metallic material, is suspended in the centre of the frame element 62" and fixed to the frame element 62" by twisting central arms 63" made of the same material as the micro-mirror, in similar manner to the micro-mirror of the embodiment relating to FIG. 2. The term "self-supporting" means that the film can support itself without the aid of a supporting substrate.

If a current is caused to flow through the winding 61", the unit formed by the arm element 51" and by the winding 61" forms an electromagnet. By modulating the current flowing through the winding 61", it is thus possible to induce a variable magnetic field proportional to the current. The vector of magnetic induction within the arm 51" (which constitutes the core of the electromagnet) is constant and is directed along the axis X of the arm 51" (magnetic circuit). At the end of the electromagnet, that is, in the region of the distal end of the arm 51", the magnetic field is arranged as for a normal dipole. The micro-mirror 52 is disposed actually in the vicinity of the last turns of the winding 61", very close to the arm element 51". Since the micro-mirror 52 is made of ferromagnetic material, the magnetic field which strikes it induces in it a magnetic polarization which subjects it to a force. This tends to cause the micro-mirror to rotate about the central arms 63", so as to align the induced dipole with the magnetic field lines, minimizing the energy of the system. As for the embodiment of FIG. 2, this rotation is actually a twisting of the central arms 63" which produce a resilient biasing force that opposes the magnetic force and tends to return the mirror to the equilibrium position (magnetic field zero). The angle of rotation is controlled by modulating the intensity of the current which passes through the winding 61", that is, by altering the magnetic induction field. By changing the direction of the current, it is also possible to reverse the direction of rotation of the micro-mirror 52.

The manufacture of the micro-mirror/frame unit is based on a conventional micro-machining technique with the use of a sacrificial layer. This sacrificial layer enables normal optical lithography and electrolytic growth techniques to be used for the production of the device, finally offering the possibility of separating the device from the substrate, rendering it completely free-standing. Once separated from the substrate, the device is fixed on the bar of ferromagnetic material by one side of the frame.

The configuration of FIGS. 5 and 6 has the advantage, in comparison with the configuration of FIG. 2, that the current does not pass through the micro-mirror 52 but only through the winding 61"; this reduces problems connected with the thermal stress of the mirror 52 (which may even be destroyed if too large a current passes through it) and thus permits the use of larger currents and consequently enables larger angles of rotation (possibly larger by several tens of degrees) to be achieved, whilst the average life of the device is much longer. Moreover, with this configuration, it is possible to select the ferromagnetic material of the arm 51" (and hence its magnetic permeability $\mu_r$) and the number of turns of the winding 61" in a manner such as to adapt the relationship between current and desired angle of rotation according to the required application.

The data relating to the measurements made with the probe units 50 are processed by the processing unit 77 so as to obtain the distances of the points measured, correlated with the images of these points received from the CCD sensors. The processing unit 77 reconstructs the outline of the internal wall of the duct measured with the use of conventional three-dimensional image management programs. This outline can easily be stored as a graphics file having, for example, a CAD format.

The three-dimensional representation obtained by the processing unit 77 can be used directly for the automatic control of the manufacture of a piece of hearing prosthesis.

The invention is not intended to be limited to the embodiments described and illustrated herein, which should be considered as examples of the apparatus for determining the internal outline of a duct or cavity and, in particular, for determining the internal impression of the auditory canal, and of the respective probe; rather, the invention may be modified with regard to shape and arrangements of parts, constructional details, and operation. For example, the distal end of the probe unit 50 may be provided with a proximity sensor which can detect a condition of excessive proximity of that end to the walls of the duct. Moreover, the apparatus may be provided with a feeler device which can detect movements of the duct as a whole which is subjected to measurement so as to improve the accuracy of the mapping. The measurements taken would in fact be processed so as to remove therefrom contributions that are due to these movements. These arrangements are particularly appropriate when the apparatus according to the invention is used to determine the internal impression of a patient's auditory canal.

The invention claimed is:

1. An apparatus for determining the internal outline of a duct or cavity, comprising:

light-emitting means (71) suitable for generating a collimated light beam, an elongate probe element (51; 51'; 51") suitable for being introduced into the duct and for guiding the collimated beam along a predetermined propagation direction, reflector means (52) supported by the probe element (51;, 51'; 51") and for deflecting the collimated beam so as to illuminate the internal wall of the duct, and for deflecting the reflected or diffused light coming from an illuminated point (P) of the internal wall so as to guide it along the probe element (51; 51'; 51"), and detection means (76) for receiving an image of the illuminated point (P), which image is correlated with the optical distance of the point from the detection means (76), and for providing a corresponding electrical signal, conoscope means (75) interposed between the receiving reflector means (52) and the detection means (76) and suitable for producing, with the light guided by the reflector means, a holographic image with concentric interference fringes which is detectable by the detection means (76), the periods of the fringes being correlated with the optical distance of the illuminated point (P), wherein the reflector means comprise a micro-mirror element (52) rotatably articulated to a distal end of the probe element (51; 51'; 51"), the micro-mirror element (52) being orientable so as to deflect the collimated beam in selectively different directions.

2. A probe for an apparatus for determining the internal outline of a duct or cavity, comprising a probe arm element (51; 51'; 51") for being introduced into the duct and supporting at its distal end a micro-mirror element (52) which can deflect a collimated light beam directed along the probe element (51; 51'; 51") so as to illuminate the internal wall of the duct, and which can deflect the reflected or diffused light coming from an illuminated point of the internal wall so as to guide it once more along the probe element (51; 51'; 51") to enable it to be received by detection means (76) of the apparatus, wherein the micro-mirror element is rotatably articulated to the probe arm element (51; 51'; 51") so as to be orientable in a radial plane relative to the probe arm element (51; 51'; 51"), wherein the micro-mirror element (52) is integral to one end of a lever element (53) articulated to the distal end of the probe arm element (51), the free end of the lever element (53) being operable by a control rod element (55) which is arranged parallel to the probe arm element (51) and can translate along its longitudinal axis.

3. A probe for an apparatus for determining the internal outline of a duct or cavity, comprising a probe arm element (51; 51"; 51") suitable for being introduced into the duct and supporting at its distal end a micro-mirror element (52) which can deflect a collimated light beam directed along the probe element (51; 51'; 51") so as to illuminate the internal wall of the duct, and which can deflect the reflected or diffused light coming from an illuminated point of the internal wall so as to guide it once more along the probe element (51; 51'; 51") to enable it to be received by detection means (76) of the apparatus, wherein the micro-mirror element is rotatably articulated to the probe arm element (51; 51'; 51") so as to be orientable in a radial plane relative to the probe arm element (51; 51'; 51"), wherein an electrical current can flow through the micro-mirror element (52) which is disposed between a pair of elongate conductor elements (65'; 66') suitable for bringing about rotation of the micro-mirror (52) as a result of the electrical currents passing through them.

4. A probe for an apparatus for determining the internal outline of a duct or cavity, comprising a probe arm element (51; 51'; 51") suitable for being introduced into the duct and supporting at its distal end a micro-mirror element (52) which can ,deflect a collimated light beam directed along the probe element (51; 51'; 51') so as to illuminate the internal wall of the duct, and which can deflect the reflected or diffused light coming from an illuminated point of the internal wall so as to guide it once more along the probe element (51; 51'; 51") to enable it to be received by detection means (76) of the apparatus, wherein the micro-mirror element is rotatably articulated to the probe arm element (F'; 51'; 51") so as to be orientable in a radial plane relative to the probe arm element (51; 51'; 51"), wherein the probe arm element (51") is made of ferromagnetic material and is wound up, along its length, by a winding (61") capable of conducting current, the micro-mirror element (52) also being made of ferromagnetic material, so that the rotation of the micro-mirror (52) is brought about by a magnetic field produced by the current passing through the winding (61").

* * * * *

UNITED STATES PATENT AND TRADEMARK OFFICE
CERTIFICATE OF CORRECTION

| | | |
|---|---|---|
| PATENT NO. | : 7,535,564 B2 | Page 1 of 1 |
| APPLICATION NO. | : 10/517657 | |
| DATED | : May 19, 2009 | |
| INVENTOR(S) | : Enzo Di Fabrizio et al. | |

It is certified that error appears in the above-identified patent and that said Letters Patent is hereby corrected as shown below:

On the Title Page, Item (54)
Please Correct the title as follows:

APPARATUS FOR DETERMINING THE INTERNAL OUTLINE OF A DUCT OR A CAVITY ~~AND IN PARTICULAR FOR DETERMINING THE INTERNAL IMPRESSION OF THE AUDITORY CANAL, A PROBE FOR THIS APPARATUS, AND REFLECTION DEVICE FOR AN OPTICAL SCANNING APPARATUS~~

Col. 8 Claim 4, line 12, delete "(F'; 51'; 51")" and insert --(51;51';51")--.

Signed and Sealed this

Twenty-second Day of September, 2009

David J. Kappos
*Director of the United States Patent and Trademark Office*

UNITED STATES PATENT AND TRADEMARK OFFICE
CERTIFICATE OF CORRECTION

PATENT NO. : 7,535,564 B2  Page 1 of 1
APPLICATION NO. : 10/517657
DATED : May 19, 2009
INVENTOR(S) : Enzo Di Fabrizio et al.

It is certified that error appears in the above-identified patent and that said Letters Patent is hereby corrected as shown below:

On the Title Page, Item (54) and Column 1, lines 1-8,
Please Correct the title as follows:

APPARATUS FOR DETERMINING THE INTERNAL OUTLINE OF A DUCT OR A CAVITY ~~AND IN PARTICULAR FOR DETERMINING THE INTERNAL IMPRESSION OF THE AUDITORY CANAL, A PROBE FOR THIS APPARATUS, AND REFLECTION DEVICE FOR AN OPTICAL SCANNING APPARATUS~~

Col. 8 Claim 4, line 12, delete "(F'; 51'; 51")" and insert --(51;51';51")--.

This certificate supersedes the Certificate of Correction issued September 22, 2009.

Signed and Sealed this

Twenty-seventh Day of October, 2009

David J. Kappos
*Director of the United States Patent and Trademark Office*